United States Patent [19]

Sandhu

[11] Patent Number: 4,530,242

[45] Date of Patent: Jul. 23, 1985

[54] MOVABLE ULTRASONIC TRANSDUCER ARRAY

[75] Inventor: Jaswinder S. Sandhu, Chicago, Ill.

[73] Assignee: Raj Technology, Inc., Chicago, Ill.

[21] Appl. No.: 516,542

[22] Filed: Jul. 25, 1983

[51] Int. Cl.³ .............................................. G01N 29/00
[52] U.S. Cl. ...................................... 73/625; 73/603; 73/619
[58] Field of Search ................ 73/619, 603, 621, 625, 73/626, 628, 633, 634; 367/7

[56] References Cited

U.S. PATENT DOCUMENTS

| | | | |
|---|---|---|---|
| 3,837,423 | 9/1974 | Mailer | 367/7 |
| 3,979,711 | 9/1976 | Maginness et al. | 73/626 |
| 4,304,133 | 12/1981 | Feamster, III et al. | 73/633 |
| 4,434,659 | 3/1984 | Kurtz et al. | 73/633 |
| 4,437,468 | 3/1984 | Sorenson et al. | 73/625 |

Primary Examiner—Howard A. Birmiel
Attorney, Agent, or Firm—Hill, Van Santen, Steadman & Simpson

[57] ABSTRACT

There is disclosed herein a movable, ultrasonic transducer array for use in an ultrasonic inspection system that employs a signal detector and display of the liquid crystal cell type. The movable array uniformly insonifies the object to be inspected and is particularly suitable for inspecting large objects or large areas of an object. The array may include a plurality of sending or emitting transducers which are held in substantially parallel alignment so that their transmission or radiation axes are parallel. The array is part of an assembly which includes a support for holding the transducers and a drive system for moving the array and support along a predetermined path.

In a first specific embodiment, the array is mounted on a support which moves along a circular path while maintaining the relative horizontal and vertical positions of the transducers. That movement is accomplished by use of a drive and linkage system which provides for an eccentric-like movement. In a second embodiment, an array is provided in which the support rotates through a circular path, but the relative horizontal and vertical positions of the transducers changes. This may be referred to as a planetary-type movement. In addition, other movements such as linear translation can be provided.

It has been found that the ultrasonic beam so generated produces a large and uniform insonifying beam.

47 Claims, 10 Drawing Figures

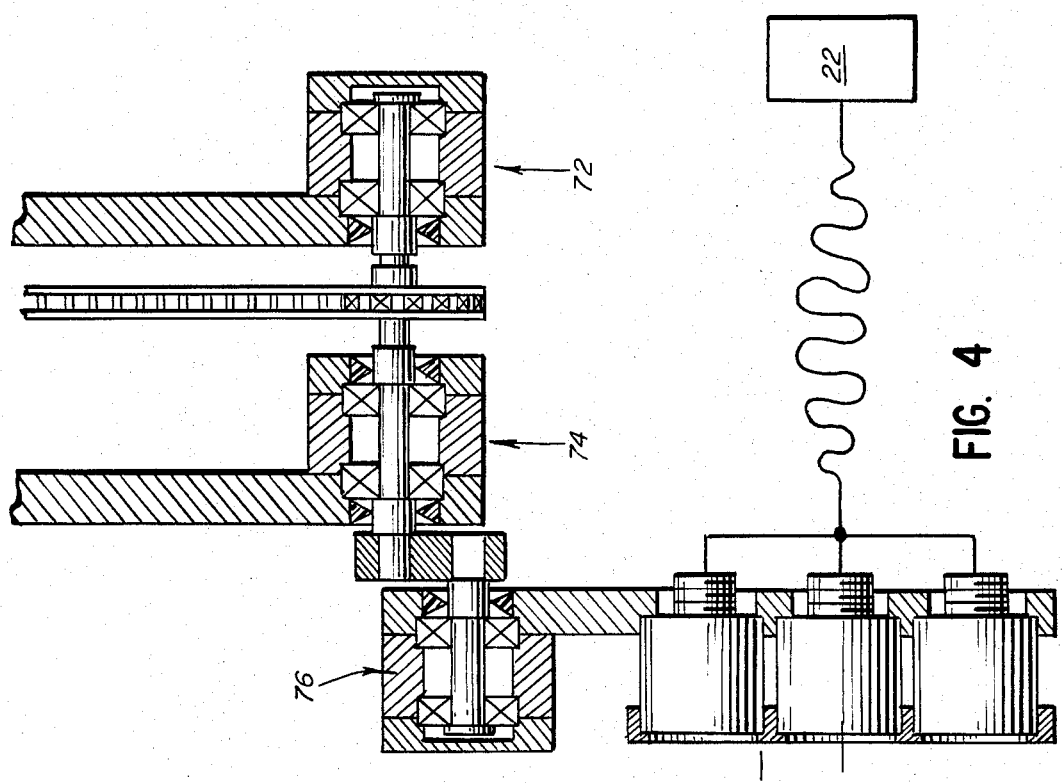
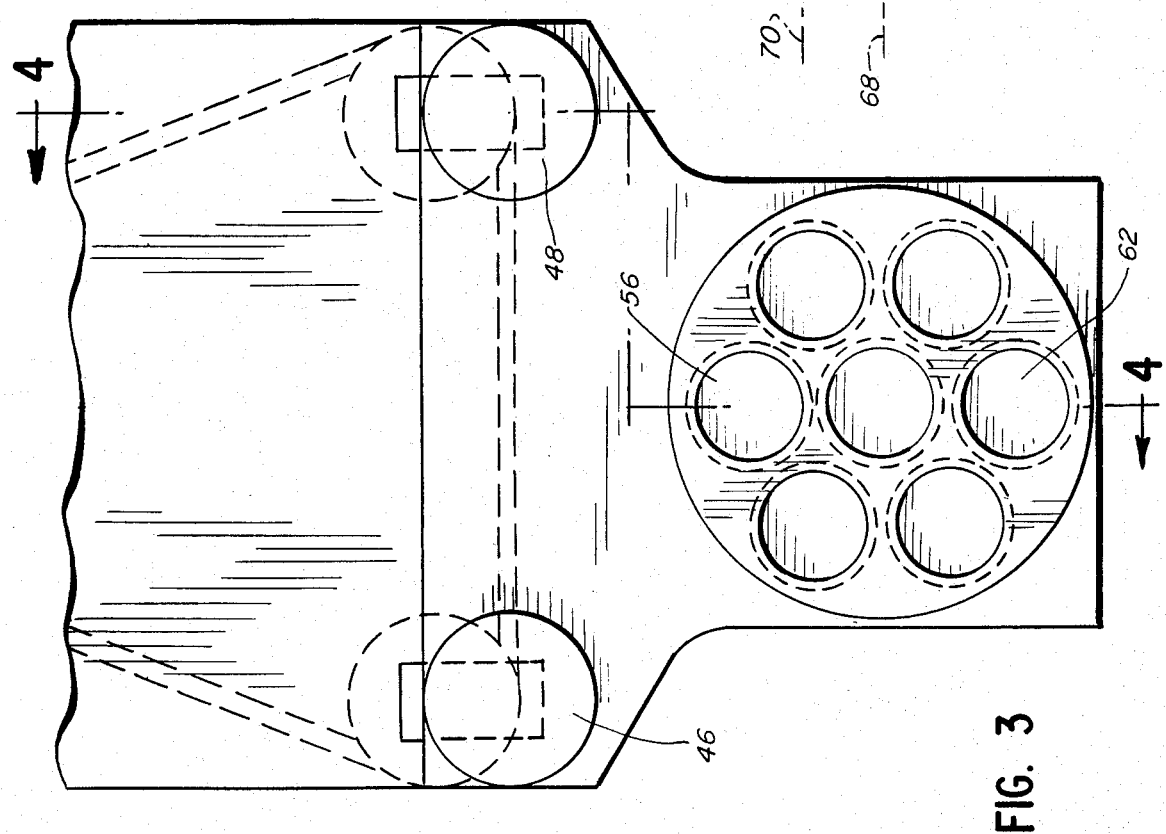
FIG. 4
FIG. 3

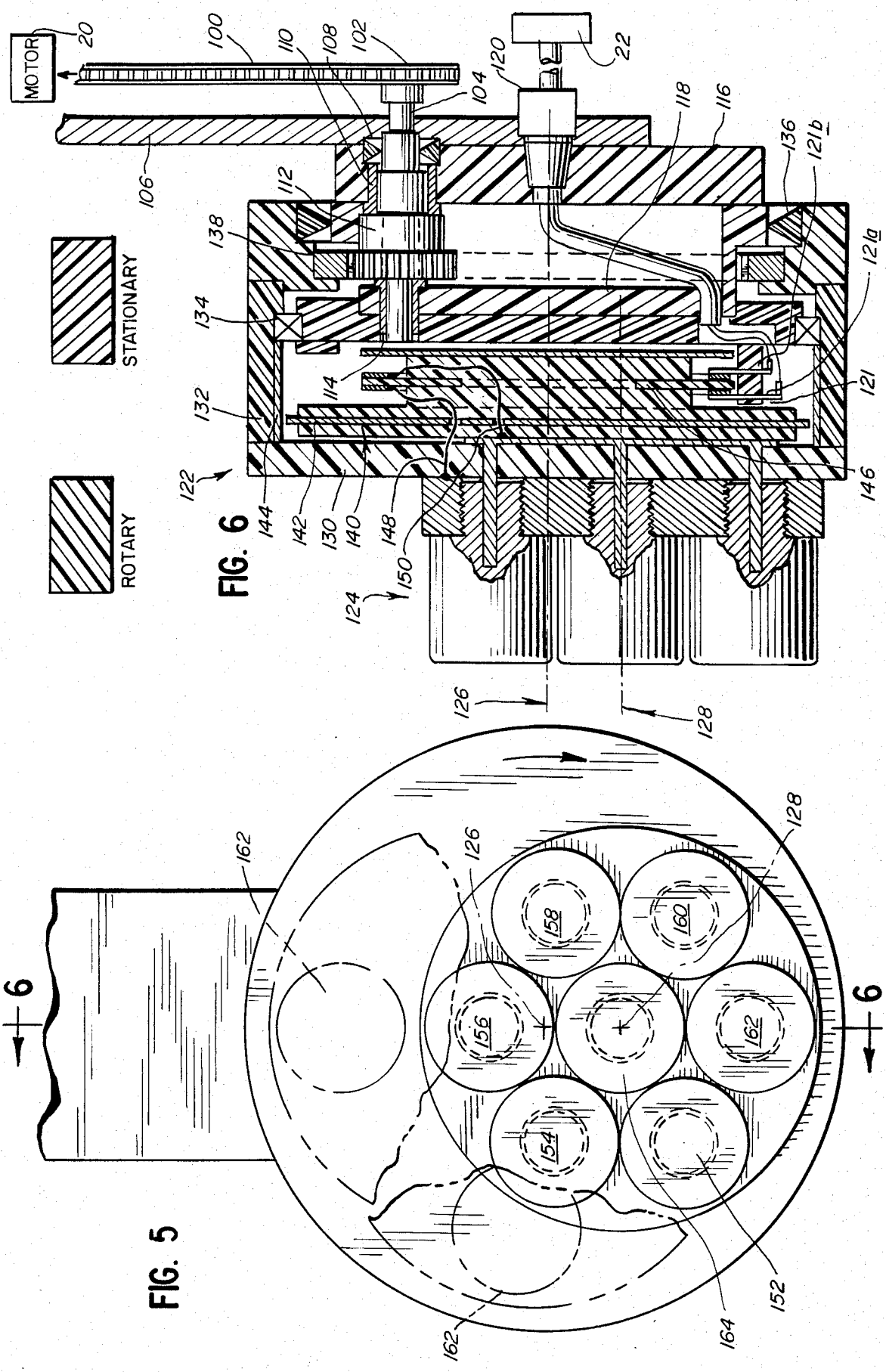

FIG. 8
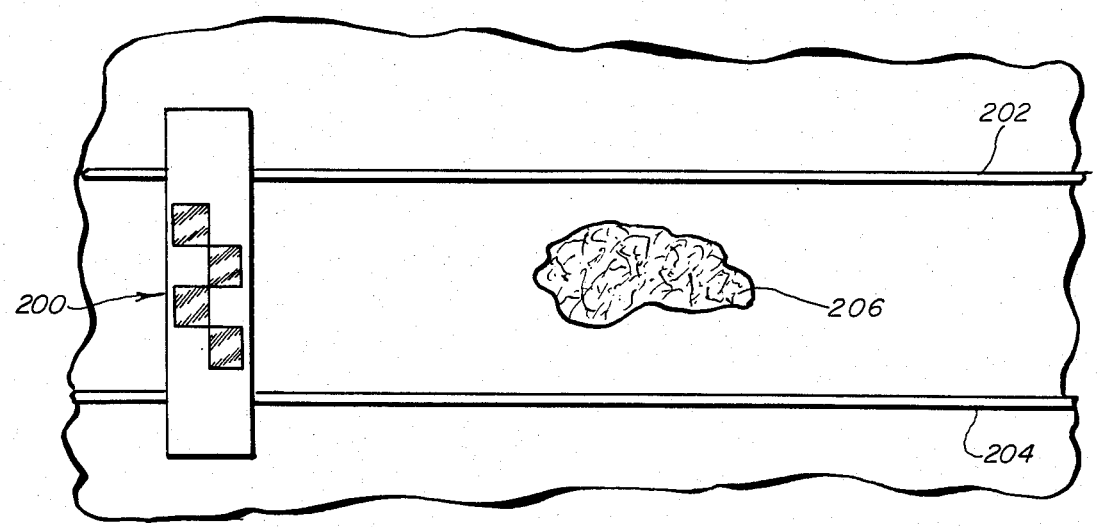
FIG. 9
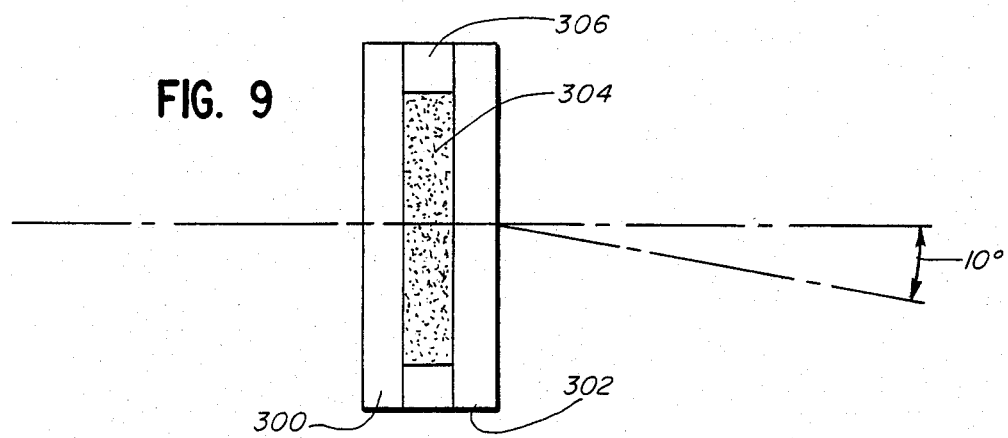
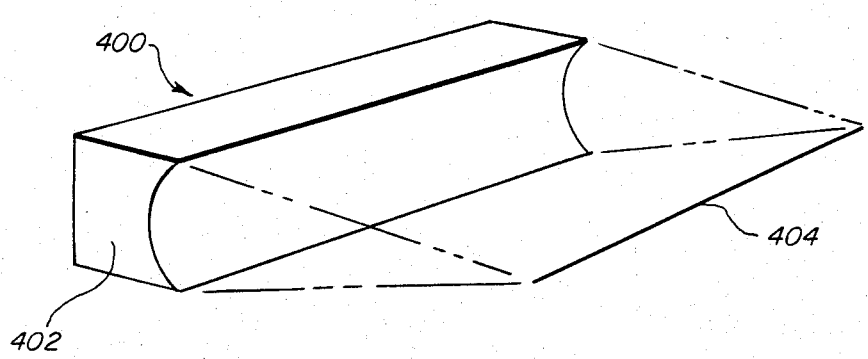
FIG. 10

MOVABLE ULTRASONIC TRANSDUCER ARRAY

BACKGROUND OF THE INVENTION

This invention relates to an apparatus and method for non-destructively inspecting various bodies or objects using a moving transducer array, specifically in combination with a liquid crystal ultrasonic detector cell.

Ultrasonic examination of various bodies or objects is well known in both the medical and industrial fields. Typically an ultrasonic transducer is provided which emits an insonifying ultrasonic beam which is directed to an object. The ultrasonic beam passes through the object, is received by a detector and an image is generated. Liquid crystal detector cells which display an image are disclosed in various U.S. patents. See, for example, U.S. Pat. Nos. 4,379,408; 4,338,821; 3,579,054; 3,707,323; 3,831,434; and 3,879,989.

In these systems, the ultrasonic transducer may be a single transducer which is held in position or a plurality of transducers held in position which are sequentially excited so as to produce an image.

However, in order to inspect a larger object, such as an aircraft wing or a fuselage section, it is necessary to provide a large and uniform ultrasonic beam. The prior single fixed position transducer or fixed position array which is sequentially excited do not provide a large uniform beam and have not produced desirable results for inspecting such objects or sections.

Rotatable wheels have been suggested for inspecting larger objects in which transducers are aligned along the radii of the wheel and are carried on the circumference or the periphery of the wheel so as to contact the object as the wheel is rolled. See for example, U.S. Pat. Nos. 3,423,994; 3,541,840; and 3,771,354. These devices are believed to be too cumbersome, not sufficiently flexible in their use and do not appear to be adaptable for use with liquid crystal detectors.

A rotating transducer array is shown in U.S. Pat. No. 3,280,621 in which the sending transducers are focused at a point on the axis of rotation and the receiving transducer is mounted on the axis of rotation for receiving reflected signals. In view of the focused nature of the beam and the fact that the maximum insonified area is limited to the profile of the array and can only be increased to that limit by moving the array toward the object, this device is not believed to be suitable for use in inspecting large objects. Furthermore, this device is not intended for use with a liquid crystal display cell.

Single transducers have been used in the pulseecho mode to scan objects and produce what are known as "C-scans". However, such systems are extremely slow to produce an image and have not been employed with the liquid crystal detector cell.

It is therefore the primary object of this invention to provide an ultrasonic signal source which is uniform, which can insonify large objects, and which can be used with liquid crystal detector cells.

This and other objects of this invention will become apparent from the following description and appended claims.

SUMMARY OF THE INVENTION

There is provided by this invention a movable, ultrasonic transducer array which is suitable for use with a liquid crystal display and which provides a large uniform insonifying beam that is suitable for use in inspecting large objects and sections of large objects such as aircraft wings, and the like.

More specifically, there may be provided a transducer array which includes a plurality of sending ultrasonic transducers mounted to a support member with the transmission or radiation axes of the transducers being in substantially parallel alignment. Drive means are provided for moving the array and support along a predetermined path in a periodic manner.

In one embodiment drive and linkage means are provided for rotating an array about an axis spaced from the geometric center of the array, but within the periphery of the array, and with the transducers maintaining their relative vertical and horizontal positions. This may be characterized as an eccentric movement of the array. In another embodiment, the array is rotated about an axis which is spaced from the geometric center of the array, but in that arrangement, the transducers do not maintain their horizontal and vertical orientations relative to each other. In this embodiment the rotation is provided by a ring and pinion gear assembly to which the transducer array is mounted and may be characterized as a planetary-type movement. The former embodiment may be characterized as maintaining the spatial relationships, i.e., relative positions, among the individual transducers unchanged, while the latter embodiment may b echaracterized as changing the spatial relationships because although the distances and angles between individual transducers remain constant, the relative positions of the transducers, i.e., above, below, to the left of, and to the right of each other, are continuously changing as the array traverses the The former embodiment may be characterized as maintaining the spatial relationships, i.e., relative positions, among the individual transducers unchanged, while the latter embodiment may be characterized as changing the spatial relationships because although the distances and angles between individual transducers remain constant, the relative positions of the transducers, i.e., above, to the left of, and to the right of each other, are continuously changing as the array traverses the path.

Horizontal and vertical translation of the array is also suitable, so long as the axis of the transmitting transducers remain parallel to prior position. By maintaining the transmission axes parallel and controlling transducer movement, the angular relation between the liquid crystal cell and incident ultrasonic radiation from the inspected body is maintained substantially constant.

Other movable transducer systems as disclosed herein may also be used.

BRIEF DESCRIPTION OF THE DRAWINGS

FIG. 3 is a front elevational view of an array which is moved eccentrically;

FIG. 4 is a sectional view taken substantially along line 4—4 of FIG. 3;

FIG. 5 is a front elevational view of a transducer array which rotates as it is moved in a circular path;

FIG. 6 is a sectional view taken along line 6—6 of FIG. 5 showing the interior of the array assembly;

FIG. 8 is a diagrammatic view showing a linear movement;

FIG. 9 is a sectional view of a typical liquid crystal cell; and

FIG. 10 is a perspective view showing a shaped transducer.

DESCRIPTION OF THE PREFERRED EMBODIMENT

Figure 1:
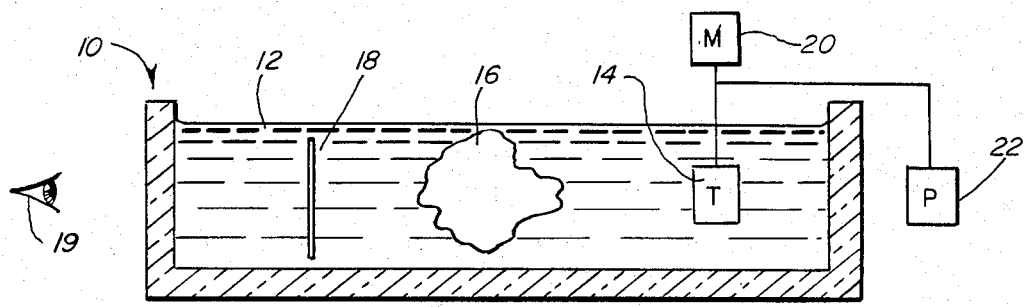
FIG. 1 is a diagrammatic view showing a typical ultrasonic inspection set-up.

Referring now to FIG. 1, there is shown a typical ultrasonic inspection apparatus 10 generally, which includes a bath 12, usually water, within which a transducer 14, an object 16, and liquid crystal detector cell 18 are positioned and acoustically coupled. The transducer 14 insonifies the object 16 and energy exiting the object is incident on the cell 18. The cell converts the incident energy to a visible image which can be seen by the viewer 19. Numerous optical systems can be provided for viewing the image and various different cell constructions can be used. For example, U.S. Pat. No. 4,379,408 discloses a laminated type of liquid crystal detector cell. The transducer 14 may be an array or plurality of transducers which is moved by a motor 20. Both the motor and transducer obtain their power from source 22.

There are several embodiments of a movable transducer array which meet the criteria for a large and uniform insonifying beam. Specific embodiments are discussed in the following sections.

It is to be noted that by moving the array, an insonifying beam cross-section is created which is larger than the stationary beam and the beam is more uniform since the movement provides an averaging effect. Averaging effect is intended to mean that each portion of the test area is insonified by acoustic energy of substantially the same intensity over an average period of time.

Array with Eccentric-Type Movement

Figure 2:
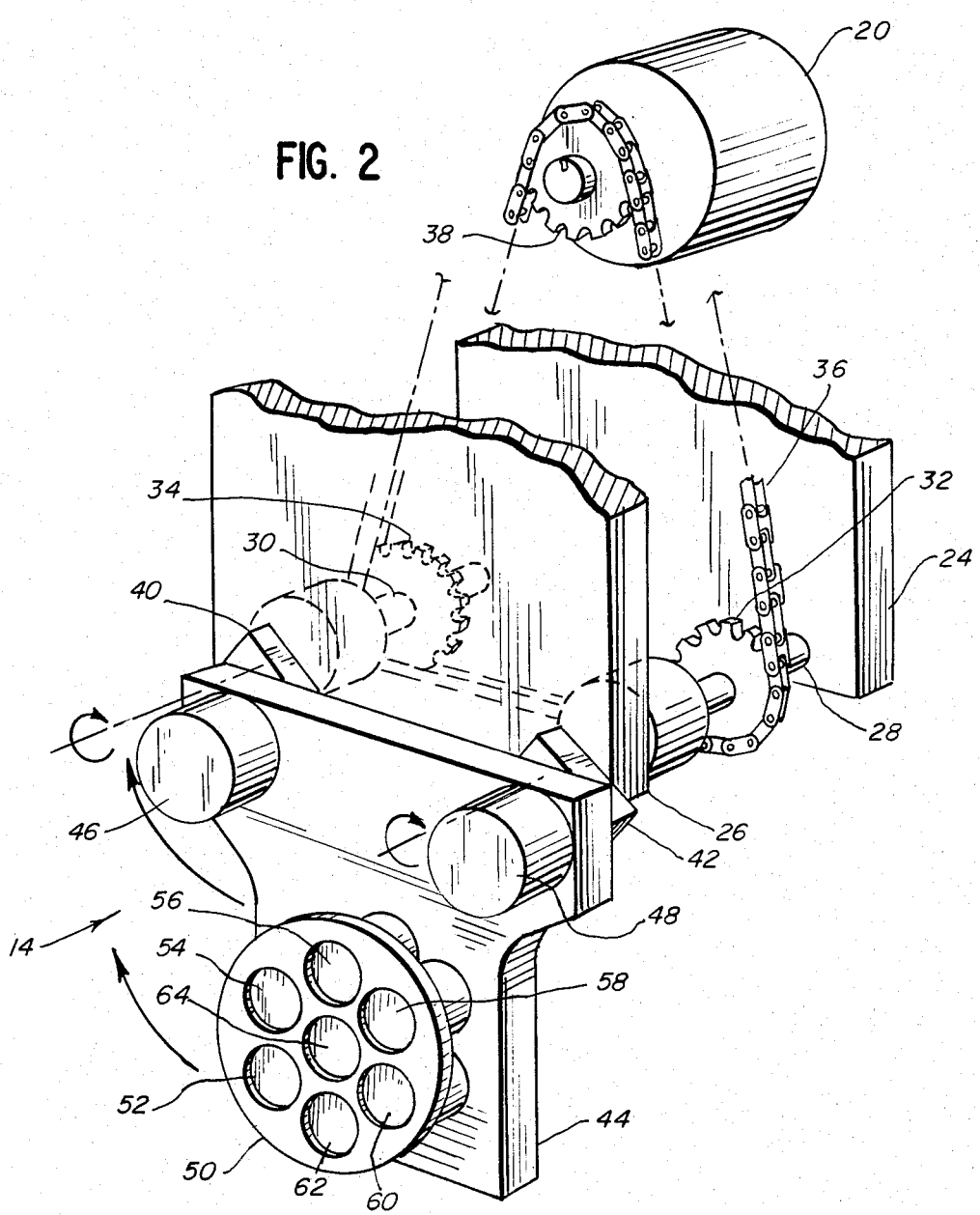
FIG. 2 is a perspective view showing an array which is moved eccentrically in a circular path.

One embodiment of a movable transducer array is shown in FIGS. 2, 3 and 4. Referring first to FIG. 2, the motor 20 and the movable transducer array assembly 14 are shown. The motor 20 is mounted to a fixed or stationary frame (not shown) as are the support plates 24 and 26. A pair of rotatable shafts 28 and 30 are journalled to the plates and each carries a sprocket gear 32 and 34. A drive chain 36 is trained about the motor drive sprocket 38 and about the driven sprockets 32 and 34. Rotation of the motor sprocket 38 drives the sprockets 32 and 34 and turns the axles or shafts 28 and 30.

A pair of links 40 and 42 are also provided and each is secured at one end to the forward terminal end of each of the axles or shafts 28 or 30. The other end of each of the links 40 and 42 is journalled to a support plate 44 via bearings 46 and 48. The support member 44 includes a disc-shaped transducer carrier 50 in which seven sending or emitting transducers 52, 54, 56, 58, 60, 62 and 64 are positioned. It will be noted that there is a central transducer and six transducers spaced thereabout in a hexagonal close-packed arrangement. As can be seen, the faces of all of the transducers lie in substantially the same plane and the radiation or transmission axis of each of the transducers are parallel to one another.

It will be appreciated that as the motor 20 operates to rotate the support plate 44, the transducer faces move in substantially the same plane and the transducer axes all remains parallel to one another. In this arrangement, it can be said that the path of movement is substantially circular and caused by the eccentric movement of the drive and linkages. Furthermore, it is seen that the geometric center of the array which passes through the center of transducer 64 is offset from the center of movement for the entire array. However, the center of movement is still within the periphery of the array itself, thus avoiding dead spots or uninsonified areas.

The parallel positioning of the axes of the transducers is seen in FIG. 4 as is the offset between the geometric center of the transducers 68 and the axis of rotation 70. FIG. 4 shows a more detailed view of the bearings 72, 74 and 76 which support the drive axles. In FIG. 3 the support plate journal points such as 46 and 48 are seen.

From FIG. 3 it will be appreciated that in this embodiment the transducers, such as 56 and 62, while they are in fact sweeping in a circular path, remain in the same vertical and horizontal or spatial relationship to each other.

It will be appreciated by virtue of the construction herein that the power source 22 can be connected directly to the transducer without twisting or damaging any of the connecting lines.

This embodiment produces a substantially uniform insonifying ultrasonic beam which is capable of insonifying large objects or sections of large objects. For example, a large graphite/epoxy panel was inspected with a beam having a 50-square inch area.

Furthermore, depending upon the particular application, the transducer radiation axes can be at an angle, perhaps 10°, to the plane of array movement, so long as all axes are substantially parallel to each other. The embodiment described herein can be used with transducers where the axes are normal to the plane of movement or skewed relative to the plane of movement.

Array With Planetary-Type Movement

Figure 7:
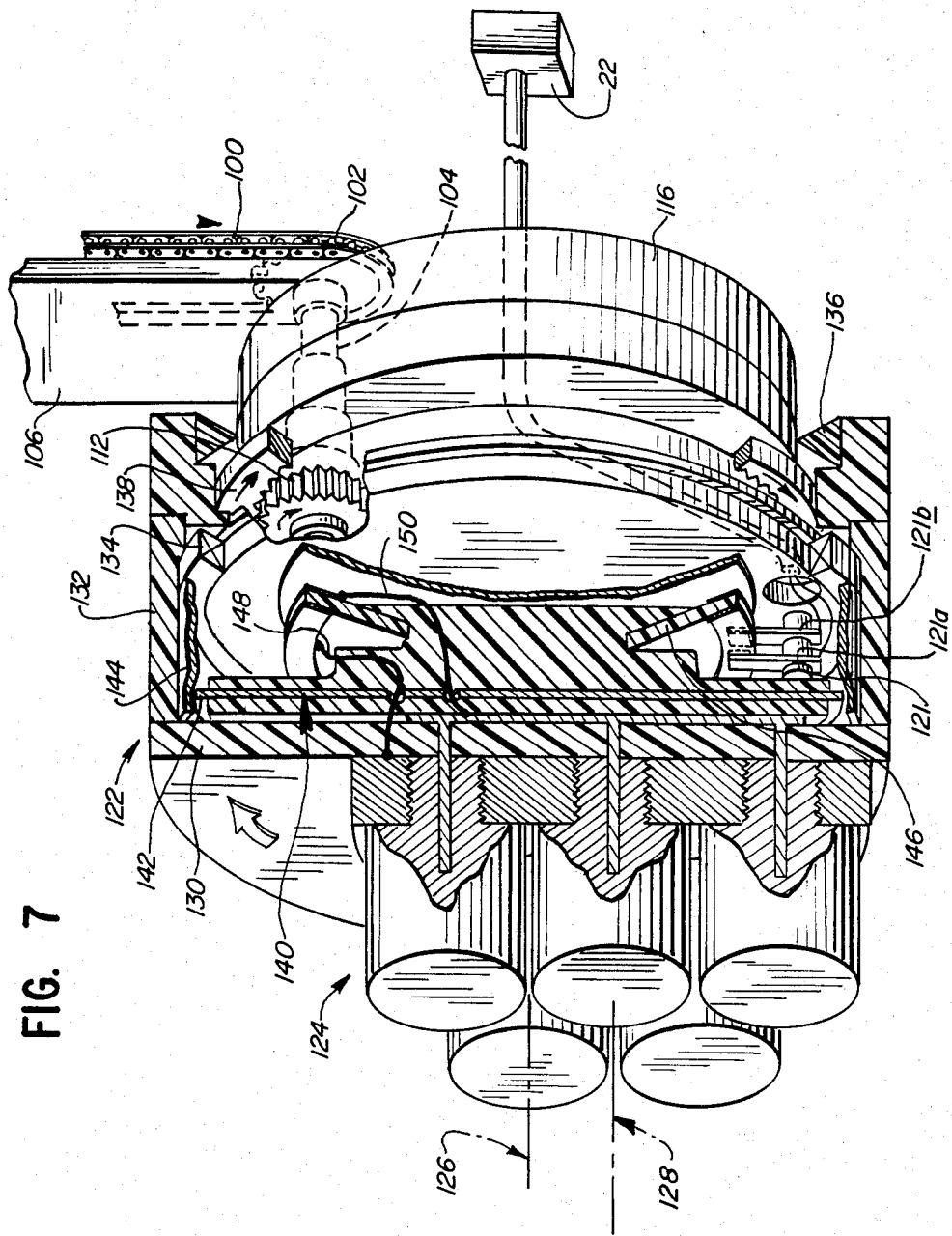
FIG. 7 is a perspective, partially elevational and partially sectional view of the array assembly of FIGS. 5 and 6.

Referring now to FIGS. 5, 6 and 7, a second embodiment for the movable transducer array is shown. In this embodiment there is again provided a drive motor 20 which drives the chain 100 that is connected to a single driven sprocket 102. The sprocket 102 is supported on a shaft 104 that is journalled and supported from a stationary support plate 106. The shaft 104 extends forwardly of the support plate 106 and carries a Neoprene seal 108, bushing 110, 24-tooth pinion gear 112, and terminates with a bushing 114. The plate 106 and shaft 104 provide a portion of a stationary section which includes the stationary back plate 116 and stationary front plate 118. The power source 22 is connected through a bushing-like structure 120 to a commutator assembly 121 which is also stationary. The commutator includes a pair of electrically conducting brushes 121a and 121b.

The foregoing elements define a stationary structure which is fixed in place relative to the frame or tank which is being used. Those elements are shown in FIG. 6 with diagonal lines extending from an upper left position to a lower right position and include plate 106, plate 116, and plate 118. The same elements are shown in elevation in FIG. 7. Thus the shaft 104 is maintained in position even though it is rotating within the stationary structure.

In order to rotate the transducers, the remaining portions of the transducer assembly array are rotatably carried on the stationary member. The rotatable portions include a cup-like housing member 122 generally, which supports the transducer array 124 generally.

As a general statement, the stationary portion remains in position and rotation of the pinion gear 112 causes the cup-like member, and thus the transducer array, to rotate about an axis. In this situation the axis of rotation 126 is spaced from the geometric center of the array 128, and so long as the center of rotation 126 is within the geometric periphery of the array, a substantially uniform or averaged beam will be provided.

Referring more specifically to the rotating member, the cup-like member 122 includes a flat front wall 130 and a cylindrical side wall 132 which extends rearwardly therefrom and encloses portions of the stationary member. The rotary member is mounted to the stationary member by a bearing 134 which is positioned between the side wall 132 and the stationary plate 118. Peripheral seals 136 are also provided to seal the interior of cup-shaped assembly.

A 96-tooth ring gear 138 is mounted to the rotary member and is positioned for engagement by the pinion gear 112. A rotating commutator or slip ring assembly 140 is provided for electrical contact with the brushes 121a and 121b. The slip ring is positioned adjacent the back edge of the front plate 130.

Metal shielding members, such as 142 and 144, are provided about the slip ring assembly so as to suppress extraneous electrical signals due to the operation of the commutator assembly 121. A copper-plated disc 146 is supported from the assembly 140 for engagement by the brushes 121a and 121b.

It will be appreciated that the disc 146 rotates with the other rotatable elements, while the power line 120 remains stationary. Thus the operation of the brushes 121a and 121b, along with the plated disc 146, provide the connection for delivering electrical power to the transducers. As is seen, electrical connections may be made by lines 148 and 150 from one side of the disc to the transducer and from the other side of the disc to a common ground.

The transducer array 126 is mounted to the front face of the plate 130 and carries seven sending or transmitting transducers 152, 154, 156, 158, 160, 162 and 164. These are arranged with a central transducer and six transducers positioned in a hexagonal close-packed arrangement thereabout.

In operation, the motor 20 drives the chain 100, which in turn causes the shaft 104 and pinion gear 112 to rotate. Rotation of the pinion gear causes the housing 122 to rotate due to the interaction of the pinion gear 112 and ring gear 138. Power is continuously supplied to the transducers via line 120 which connects to the commutator assembly 121, and in turn to the slip ring disc 146 and through lines 148 and 150 to common connections through the transducer.

The axis of rotation for the rotating portion of the housing is at the center of the ring gear which is indicated by the axis 126. As the array is rotated in a circular path, the transducers also change their relative or spatial positions. This is unlike the first described embodiment. More specifically, the transducer 162, which is shown at the 6 o'clock position in FIG. 5, will move to the 9 o'clock position, and then the 12 o'clock position as shown by dotted lines in FIG. 5. This is in a sense a planetary-type of movement.

In this embodiment the radiation axes are parallel to each other and normal to the plane or rotation.

The speed of rotation for the arrays shown in FIGS. 2-4 and FIGS. 5-7 can be adjusted to fit individual conditions. Furthermore, while the hexagonal close-packed transducer arrangement is particularly useful for cylindrical or circular transducers, other arrangements may be used as can transducers having other shapes such as square or rectangular.

Alternative Embodiments

In addition to the embodiments shown herein where the motion of the array is principally circular and about a predetermined centerline, it will be understood that a number of other motions along a closed path and which are periodic in nature can be used. For example, an elliptical motion could be produced, a square motion could be produced, and in both cases, the movement of the transducers is along a closed and predetermined path and is periodic in nature. In other words, there is a definable cycle to the movement of the transducers along whatever path is selected.

In addition to the closed path, there can be movement along a predetermined path, such as a linear path or a curved path. For example, the transducers could be moved along a horizontal line from one extreme to a second extreme and then back. In FIG. 8 an array 200 of four square transducers can be moved back and forth along rails, such as 202 and 204, to scan the object 206. Numerous of these types of paths can be defined depending upon the nature of the particular application.

It is anticipated that combinations of the arrays of FIGS. 2-4, 5-7 and 8 may be used. For example, a rotating array of the type in FIGS. 2-4 or 5-7 may be mounted on a carriage and moved linearly as in FIG. 8. Moreover, arrays which spin about their own center axis may be suitable when the transducers are selected and arranged to avoid dead or uninsonified spots.

In the embodiments shown in FIGS. 2-8, each array is shown employing a plurality of similar transducers. As shown, the transducers in each array are similar in size, shape, and operating characteristics. Depending upon the application, transducers of different sizes and shapes can be used in the same array. This necessarily means different operating characteristics. However, in all of the arrays the transmission frequency will be substantially the same. In addition, while the transducer radiation axes are parallel to each other, they may be either normal to or skewed relative to the plane of movement. If skewed, they must maintain the same angular relationship to the plane throughout the movement.

In all of the embodiments, it is understood that a liquid crystal detector cell is positioned behind the object so as to receive ultrasonic radiation passing through the object.

A typical liquid crystal cell is shown in FIG. 9 and includes a pair of acoustically transparent cover plates or substrates 300 and 302, at least one of which is optically transparent. A liquid crystal material 304, such as MBBA, is sealed between the covers by the peripheral seal 306. Specific details of such cells are disclosed in patents, such as U.S. Pat. No. 4,379,408. These cells retain the image formed thereon for a period of time after the signal is removed. Thus the cell parameters, scanning speed of the moving transducers array, and angular relationship between the insonifying beam and cell need to be matched so as to assure a high-quality, continuous, non-flickering image. More specifically, image rise and decay times are used in selecting transducer scanning speeds.

Furthermore, the insonifying beam can strike the cell normal to its surface or within an angular range, which is dependent upon the cell constructions (e.g., $\pm 10°$) and provide a high-quality image. The particular acceptable angular variation is dependent on the particular cell and is selected to assure substantial acoustic transmission into the cell and through the cell substrates.

Again, the angular relationship of the transducers to the cell must be matched in order to maximize performance. However, the axes of transmission of the individual transducers are maintained substantially parallel to each other.

In all of the previously described embodiments, the angular relationship between the transducer radiation axes and the liquid crystal cell surface has remained constant and did not vary.

Furthermore, single transducers may be used for scanning. For example, there is shown in FIG. 10 a transducer where the beam forms a line that sweeps an object. Such a transducer is shown as 400, has a concave face 402 and generates a line beam 404 that can sweep an object. Such a transducer can be moved linearly, as shown in FIG. 8, and its movement timed to the cell construction.

Substantially uniform beams and images have been produced using embodiments discussed herein.

It will be appreciated that numerous changes and modifications can be made to the embodiments described herein without departing from the spirit and scope of this invention.

What is claimed is:

1. An ultrasonic inspection apparatus which includes a plurality of ultrasonic transducer elements arranged in an array with all radiation axes of said transducer elements being in substantially parallel alignment for insonifying an object to be inspected, liquid crystal detector cell means for receiving ultrasonic energy from an inspected object and displaying an image, and means for moving said ultrasonic transducer means in a plane in a predetermined and periodic manner so as to scan and insonify objects having a size greater than the cross-section of the stationary ultrasonic beams, said radiation axes of said transducer elements being skewed relative to said plane and relative to said liquid crystal detector cell means.

2. An ultrasonic inspection system as in claim 1, wherein said cell is characterized by an image rise and decay time and said rate of transducer movement is matched to said rise and decay time.

3. An ultrasonic inspection system as in claim 1, wherein said ultrasonic energy is incident on said cell at angles matched to the cell construction so as to assure substantial acoustic transmission into said cell.

4. An ultrasonic apparatus as in claim 1, wherein there is further provided motor and linkage means operatively associated with said array for moving said array along said predetermined path.

5. An ultrasonic inspection apparatus as in claim 1, wherein the angular relationship between the ultrasonic radiation incident on said cell and said cell remains substantially constant as said transducer beam is moved.

6. An ultrasonic inspection apparatus which includes a plurality of ultrasonic transducer elements with all radiation axes of said transducer elements being in substantially parallel alignment for insonifying an object to be inspected, liquid crystal detector cell means for receiving ultrasonic energy from an inspected object and displaying an image, and means for rotating said array about an axis in a plane in a predetermined and periodic manner so as to scan and insonify objects having a size greater than the cross-section of the stationary ultrasonic beams.

7. An apparatus as in claim 6, wherein said array rotates about an axis spaced from the geometric center of the array but within the periphery of the array.

8. A movable ultrasonic transducer array assembly for providing uniform insonification of an object to be inspected, said assembly including:
    means for supporting a plurality of sending transducers in substantially parallel alignment;
    a plurality of sending transducer means mounted to said support means in an array having a periphery with each of their transmission axes being substantially parallel to each other; and
    means for moving said array and support along a predetermined planar closed loop path having a geometric center within said periphery in a periodic manner.

9. An array as in claim 8, wherein there is further provided motor and linkage means operatively associated with said array and support for moving said array and support through an enclosed path without changing the relative spatial relationship of said transducers.

10. An array as in claim 9, wherein said path is a substantially circular path.

11. An array as in claim 10, wherein said motor and linkage means moves said array and support in an eccentric-like manner and wherein the center of rotation is spaced from the center of said array.

12. An array as in claim 11, wherein said drive and linkage means includes a pair of spaced and elongated link means rotatably connected at one end to said support, a pair of drive axles connected to the other end of said linkages for rotating said linkages in unison and thereby rotating said array, and drive means connected to said axles for rotating said axles.

13. An array as in claim 12, wherein said each of said axles carry a pinion gear, said drive carries a sprocket, and a chain drivingly interconnects the sprocket and pinion gears.

14. An array as in claim 8, wherein there is further provided drive and gear means operatively associated with said array and support for moving said array and support through an enclosed path wherein the relative spatial relationships of the transducer changes.

15. An array as in claim 14, wherein said path is a substantially circular path.

16. A method for ultrasonically inspecting large objects and sections of large objects by insonifying an object with acoustic energy and receiving acoustic energy from the object on a liquid crystal detector cell which forms a viewable image, said method comprising the steps of:
    providing a source of acoustic energy having a periphery, an object to be inspected and a liquid crystal detector cell;
    acoustically coupling said source to said object so as to insonify said object; and
    moving said source around a planar closed loop path having a geometric center within said periphery while maintaining the axes of transmission of said source parallel at each position of movement for increasing the effective size of the beam and creating a uniform beam.

17. A method as in claim 16, wherein said source is moved in a substantially circular path.

18. A method as in claim 16, wherein the rate of movement of said source is matched to the characteristics of said liquid crystal cell.

19. An ultrasonic inspection apparatus comprising:
   an ultrasonic transducer means for insonifying an object to be inspected, said ultrasonic transducer means having a Periphery;
   a substantially planar detector means for receiving ultrasonic energy from an inspected object and converting said ultrasonic energy to a viewable image; and
   a means for moving said ultrasonic transmission means in a planar closed loop path having a geometric center, said geometric center being disposed within said periphery for uniformly insonifying an object larger than said periphery.

20. An ultrasonic inspection apparatus as claimed in claim 19, wherein said planar closed loop path is a circle.

21. An ultrasonic inspection apparatus as claimed in claim 20, wherein said means for moving moves said ultrasonic transmission means around said closed loop path in equal repeated periods.

22. An ultrasonic inspection apparatus as claimed in claim 19, further comprising a support member on which said ultrasonic transmission means is mounted, and wherein said means for moving said ultrasonic transducer means comprises:
   a prime mover having a drive shaft; and
   a linkage drivingly connecting said drive shaft to said support member.

23. An ultrasonic inspection apparatus as claimed in claim 22, wherein said linkage comprises:
   a first sprocket mounted on said drive shaft for co-rotation therewith;
   second and third spaced sprockets respectively rotatably mounted in first and second sprocket bearing units, each bearing unit having a central axis; a driven chain entrained about said first, second and third sprockets; and
   first and second connecting members respectively rotatably connecting said first and second sprocket bearing units to said support member at points on said support member which are respectively equadistantly offset from the respective center axes of said first and second bearing units.

24. An ultrasonic inspection apparatus as claimed in claim 22, wherein said linkage comprises a gear arrangement having a stationary gear drivingly connected to said prime mover and a rotated gear engaging said stationary gear and connected to said support member, said rotated gear having an axis of rotation offset from the axis of rotation of said stationary gear.

25. An ultrasonic inspection apparatus as claimed in claim 24, wherein said rotated gear is a ring gear.

26. An ultrasonic inspection apparatus as claimed in claim 25, wherein said ring gear has interiorly disposed teeth and wherein said stationary gear is disposed in the interior of said ring gear meshing with said teeth.

27. An ultrasonic inspection apparatus as claimed in claim 24 for use with a source of electric power for said ultrasonic transducer means and further comprising:
   a stationary brush element electrically connected to said electric power source; and
   an electrically conducting ring connected to said support element for co-rotation therewith and electrically connected to said ultrasonic transducer means, said ring rotating past said stationary brush element in sliding engagement therewith for transmitting electric power from said source to said 28. An ultrasonic inspection apparatus as claimed in claim 19, wherein said ultrasonic transducer means is an array having a plurality of individual transducer elements, each transducer element having a radiation axis and said radiation axes being substantially parallel.

29. An ultrasonic inspection apparatus as claimed in claim 28, wherein said radiation axes are skewed with respect to the plane containing said closed loop path.

30. An ultrasonic inspection apparatus as claimed in claim 28, wherein said radiation axes are normal to the plane containing said closed loop path.

31. An ultrasonic inspection apparatus as claimed in claim 28, wherein said array has seven individual ultrasonic transducer elements including a centrally disposed transducer element and six transducer elements equadistantly disposed around said centrally disposed transducer element at the respective corners of a hexagon.

32. An ultrasonic inspection apparatus comprising:
   an ultrasonic transducer array for insonifying an object to be inspected, said array having a periphery;
   a support member on which said array is mounted;
   a prime mover having a drive shaft with a first sprocket mounted thereon for co-rotation therewith;
   first and second space bearing units each having a central axis;
   second and third sprockets respectively rotatably supported by said first and second bearing units;
   a driver chain entrained about said first, second and third sprockets;
   first and second connectors respectively connecting said first and second bearing units to said support member at points on said support member which are respectively equadistantly offset from the respective central axes of said first and second bearing units for rotating said support member and said array in a planar closed loop path having a geometric center within said periphery of said array for uniformly insonifying an object larger than said periphery; and
   a substantially planar detector means for receiving ultrasonic energy from an inspected object and converting said ultrasonic energy into a viewable image.

33. An ultrasonic inspection apparatus for use with an electric power source comprising:
   an ultrasonic transducer array for insonifying an object to be inspected, said array having a periphery;
   a housing having an exterior on which said ultrasonic transducer array is mounted;
   a prime mover having a drive shaft in driving connection with a driven gear;
   a ring gear mounted in the interior of said housing for co-rotation therewith, said ring gear having interiorly disposed teeth and said driven gear being disposed in the interior of said ring gear in meshing engagement with said teeth for rotating said housing and said array in a planar closed loop path having a geometric center disposed within said periphery of said array for uniformly insonifying an object to be inspected which is larger than said periphery;
   a stationary brush element disposed in the interior of said housing and electrically connected to said electric power source;

an electrically conductive ring mounted in the interior of said housing for co-rotation therewith and electrically connected to said ultrasonic transducer array, said ring disposed for rotating past said stationary brush element in sliding engagement therewith for transmitting electric power from said source to said ultrasonic transducer array through said ring; and a substantially planar detector means for receiving ultrasonic energy from an inspected object and converting said ultrasonic energy into a viewable image.

34. A method for ultrasonically inspecting an object utilizing an ultrasonic transducer array, said array having a periphery which is smaller than the object to be inspected, said method comprising the steps of:

insonifying said object to be inspected with said ultrasonic transducer array;

moving said ultrasonic transducer array around a planar closed loop path having a geometric center which is disposed within said periphery;

detecting ultrasonic energy from the object to be inspected; and converting the detected ultrasonic energy into a viewable image.

35. A method for ultrasonically inspecting an object as claimed in claim 34, wherein the step of moving said ultrasonic transducer array around a planar closed loop path is further defined by moving said ultrasonic transducer array around a circle.

36. A method for ultrasonically inspecting an object as claimed in claim 34, wherein the step of moving said ultrasonic transducer array around a planar closed loop path is further defined by moving said ultrasonic transducer array around an ellipse.

37. A method for ultrasonically inspecting an object as claimed in claim 34, wherein the step of moving said ultrasonic transducer array around a planar closed loop path is further defined by moving said ultrasonic transducer array around a planar closed loop path in equal repeated periods.

38. An ultrasonic inspection apparatus comprising:

transducer means for insonifying an object to be inspected;

a liquid crystal cell detector for receiving ultrasonic energy from said object and converting said energy into a viewable image of said object, said liquid crystal cell detector having an image decay time; and means for moving said transducer means in a predetermined repeated path having a period less than said image decay time.

39. An ultrasonic inspection apparatus as claimed in claim 38, wherein said transducer means is a transducer array having a plurality of transducer elements each having a radiation axis, said radiation axes being in parallel alignment.

40. An ultrasonic inspection apparatus as claimed in claim 38, wherein said transducer means has a radiation axis and wherein said transducer means is moved by said means for moving with said radiation axis normal to said path.

41. An ultrasonic inspection apparatus as claimed in claim 38, wherein said transducer means has a radiation axis and wherein said transducer means is moved by said means for moving with said radiation axis skewed with respect to said path.

42. An ultrasonic apparatus as in claim 38, wherein said array is moved along a substantially linear path.

43. An apparatus as in claim 42, wherein said transucer means comprises an elongated transducer having a concave surface for generating an ultrasonic beam which narrows to a line and means for moving said transducer means.

44. A method for ultrasonically inspecting an object comprising the steps of:

insonifying an object to be inspected with a transducer means;

detecting ultrasonic energy from said object with a liquid crystal detector cell having an image decay time and converting said energy into a viewable image of said objects; and moving said transducer means in a predetermined repeated path having a period less than said image decay time while insonifying said object.

45. A method as claimed in claim 44, wherein said predetermined path is a straight line.

46. A method as claimed in claim 44, wherein said predetermined path is a circle.

47. A method as claimed in claim 44, wherein said predetermined path is an ellipse.

* * * * *